United States Patent [19]

Mueller et al.

[11] Patent Number: 4,599,466

[45] Date of Patent: Jul. 8, 1986

[54] PREPARATION OF ALKANEDIOLS

[75] Inventors: Herbert Mueller, Frankenthal; Wolfgang Reiss, Ludwigshafen, both of Fed. Rep. of Germany

[73] Assignee: BASF Aktiengesellschaft, Ludwigshafen, Fed. Rep. of Germany

[21] Appl. No.: 786,614

[22] Filed: Oct. 11, 1985

[30] Foreign Application Priority Data

Oct. 12, 1984 [DE] Fed. Rep. of Germany ....... 3437429
Dec. 1, 1984 [DE] Fed. Rep. of Germany ....... 3443966

[51] Int. Cl.$^4$ .................. C07C 29/17; C07C 31/20
[52] U.S. Cl. ................................. 568/861; 568/885
[58] Field of Search ........................... 568/861

[56] References Cited

U.S. PATENT DOCUMENTS

| | | | |
|---|---|---|---|
| 2,023,383 | 12/1935 | Schrauth et al. | 568/885 |
| 2,340,687 | 2/1944 | Richardson et al. | 568/885 |
| 2,340,688 | 2/1944 | Richardson et al. | 568/885 |
| 3,184,513 | 5/1965 | Moore, Jr. et al. | 568/861 |
| 3,449,445 | 6/1969 | Wetherill | 568/861 |
| 4,011,277 | 3/1977 | Nishida et al. | 568/861 |
| 4,048,116 | 9/1977 | Voges et al. | 568/861 |
| 4,153,578 | 5/1979 | De Thomas et al. | 568/861 |
| 4,182,919 | 1/1980 | Mabuchi et al. | 568/861 |
| 4,213,000 | 7/1980 | Coates | 568/861 |

FOREIGN PATENT DOCUMENTS 2536273 2/1977 Fed. Rep. of Germany.

*Primary Examiner*—J. E. Evans
*Attorney, Agent, or Firm*—John H. Shurtleff

[57] ABSTRACT

Very pure alkanediols are prepared by catalytic hydrogenation of an alkynediol in an aqueous medium under a pressure greater than 20 bar and at above 200° C.

7 Claims, No Drawings

PREPARATION OF ALKANEDIOLS

The present invention relates to a process for the preparation of alkanediols by hydrogenating alkynediols.

Alkanediols, such as butane-1,4-diol, can be prepared by catalytic hydrogenation of alkynediols, such as butyne-1,4-diol. This process, which is described in, for example, German Pat. No. 890,944 and U.S. Pat. No. 4,153,578, employs, for example, nickel or cobalt catalysts, which are used either as Raney metals or as supported catalysts. Supported catalysts which contain not only nickel but also copper, aluminum and manganese have also been proposed for the hydrogenation of acetylenic alcohols (cf. German Laid-open Applications DOS 2,145,297 and DOS 2,004,611 and U.S. Pat. No. 3,449,445).

German Laid-Open Application DOS 2,536,273 describes a fixed-bed nickel catalyst which additionally contains the elements copper, manganese and molybdenum Although these catalysts possess longer lives than the conventional catalysts in the hydrogenation of butyne-1,4-diol to butane-1,4-diol, the results are still unsatisfactory. In order to obtain a butanediol which meets the high purity requirements, it is necessary to choose relatively high hydrogen pressures and temperatures, since only in this way can the carbonyl compounds and their derivatives, which have an adverse effect in many applications, be removed by reduction to an extent sufficient to make their harmful effect tolerable. However, increasing the harshness of the reaction conditions in this way promotes the undesirable formation of butanol and reduces the yield. At the same time, a larger amount of the undesirable by-product 2-methylbutanediol is obtained (cf. U.S. Pat. No. 4,153,578). Finally, the catalyst containing the active metals is difficult to prepare in a reproducible manner, with the same activity and life.

For the hydrogenation of the alkynols, catalysts are used in suspended form or as a fixed bed. A distinction is made between the single-stage hydrogenation, in which hydrogenation is effected in a single pass through a reactor, and the two-stage procedure. In the latter (U.S. Pat. No. 4,153,578), incomplete hydrogenation is carried out in the first stage under a low pressure and at a low temperature. Some of the alkynol or the carbonyl compounds present in the feed remain unconverted. Complete hydrogenation takes place only in the subsequent reaction zone, in which hydrogen pressures of above 200 bar and temperatures greater than 100° C. are employed.

Since butane-1,4-diol is used in large amounts industrially, the hydrogenation of but-2-yne-1,4-diol has become particularly important. In principle, the reaction can be carried out under pressures up to 400 bar. Pressures below 150 bar give a butanediol whose purity does not meet the higher practical requirements. Hence, hydrogenation is carried out under from 200 to 350 bar. Low pressures and high temperatures during the hydrogenation promote the formation of butanol, while high pressures necessitate a more expensive hydrogenation apparatus. In the conventional industrial processes over fixed-bed catalysts, the hydrogenation temperatures are from 70° C. at the entrance of the reactor to 160° C. at its exit. Initial teperatures below 70° C. are regarded as uneconomical since excessively long catalyst zones are required in order to reach the initiation temperature, while temperatures above 160° C. have a substantial adverse effect on the life of the supported catalyst, which in any case is relatively short. Although hydrogenation at high temperatures gives a high-quality butanediol, the yield decreases with increasing temperature. The fact that the hydrogenation temperatures must not be allowed to exceed 150° C. is well known and is observed in industry, since otherwise formation of butanol increases disproportionately at the expense of butanediol (cf. Ann. der Chemie, 596 (1955), pages 41 and 42, and German Laid-Open Application DOS 2,004,611, page 5, paragraph 3). Higher temperatures should also be avoided since, owing to the alkali metal salts present in the crude solutions being hydrogenated, they promote the Favorskii rearrangement (cf. Houben-Weyl, Methoden der organischen Chemie, volume 5, part 2a, page 650).

A particularly difficult task in the hydrogenation of butynediol to butanediol in the Reppe process is the removal of carbonyl compounds or their acetals. Butynediol solutions always contain significant amounts of formaldehyde which originate from the preparation and seriously interfere with the hydrogenation of the butynediol or result in the formation of undesirable byproducts. It has therefore been proposed to remove this formaldehyde from the crude butynediol solutions by distillation prior to hydrogenation (cf. U.S. Pat. No. 3,449,445, column 2, lines 57 to 60, and U.S. Pat. No. 2,993,708). In order to avoid the harmful effect of the formaldehyde, U.S. Pat. No. 4,180,687 even proposes polymerizing the formaldehyde in the crude butynediol solution by means of a strong alkali in order to render the formaldehyde harmless in the hydrogenation. Apart from poisoning the hydrogenation catalyst, the formaldehyde results in the formation of 2-methylbutane-1,4-diol from butynediol during the hydrogenation. The presence of 2-methylbutane-1,4-diol in the pure butanediol is very undesirable; furthermore, it is scarcely possible to separate 2-methylbutane-1,4-diol from the desired product butane-1,4-diol by distillation. U.S. Pat. No. 4,153,578 therefore proposes first substantially hydrogenating the butynediol solution under a low pressure and at a low temperature and then, in a second stage, completing the hydrogenation over a special molybdenum-containing Raney nickel. This makes it possible to reduce the content of methylbutanediol in the butanediol from the usual value of 1.5–2% to 0.3–0.6% at best. Such a process is technically complicated and entails substantial costs.

None of the hydrogenation processes has been able to solve a serious problem in the preparation of butanediol from butynediol solution. It is known that butynediol solutions contain not only free formaldehyde but also more than 0.2% by weight of polyoxymethylenes, these substances originating from the preparation. These compounds may coat the active catalyst surfaces and thus have an adverse effect on the hydrogenating activity or be present as a useless residue whose removal during the working up of the crude butanediol solution by distillation entails costs. We have also found that the lower polyoxymethylenes may be present as impurities in the purified butanediol unless working up by distillation is carried out by a very technically complicated procedure. Such butanediol is unsuitable, for example, for the preparation of tetrahydrofuran (by dehydration of butanediol), the polyoxymethylenes reducing the activity of the dehydration catalysts.

It is an object of the present invention to provide a process for the hydrogenation of acetylenic alcohols which not only permits a high throughput but also overcomes the disadvantage of high catalysts costs which are due to the limited life of supported catalysts or the high production costs of unsupported catalysts. At the same time, the process should give very pure alkanediols and permit hydrogenation of but-2-yne-1,4-diol to be effected with a yield of from 99 to 100%. Moreover, the process should permit by-products present in the but-2-yne-1,4-diol, eg. hydroxybutyraldehyde, acetals derived from this and acetals of butynediol, to be converted to butane-1,4-diol. A further requirement of the hydrogenation process is that the formaldehyde present in the feed of the alkynediol solutions, and its polymers, be converted to methanol. The hydrogenation of the formaldehyde polymers is in fact important in that it makes a very decisive contribution toward simplifying the purification of the butanediol by distillation, and the yield of the secondary product methanol significantly improves the cost-efficiency of the process. The novel hydrogenation process must also give very pure alkanediols which can be used in the high polymer sector or for the preparation of cyclic ethers, such as tetrahydrofuran. For example, it is desirable to prepare a tetrahydrofuran which is capable of being polymerized to polytetrahydrofuran without additional purification.

We have found that this object is achieved if alkanediols are prepared by catalytic hydrogenation of an alkynediol in an aqueous medium and in the presence of a hydrogenation catalyst under a hydrogen partial pressure of above 20 bar by a process in which the hydrogenation is carried out at above 200° C.

The novel process is distinguished in particular by the fact that it permits hydrogenation of but-2-yne-1,4-diol to butane-1,4-diol in virtually quantitative yield and gives an extremely pure end product. The butanediol is free of carbonyl functions or traces of olefinically unsaturated compounds. Even in the direct product of the process, the content of methylbutanediol is less than 0.1% by weight. The residue in this crude butanediol solution is less than 0.2% by weight, whereas the corresponding figure for the crude butanediol solutions obtained in the conventional hydrogenation process is from 1 to 2% by weight. The novel process is very cost-efficient because it permits the heat of hydrogenation produced in the reaction to be recovered at a high temperature.

Examples of alkanediols which are used for the process of the invention are those of 3 to 6 carbon atoms, such as prop-2-yn-1-ol, but-2-yne-1,4-diol and hex-3-yne-2,5-diol. The hydrogenation of but-2-yne-1,4-diol to butane-1,4-diol is of particular industrial importance.

In the novel process, the alkynediols are hydrogenated in an aqueous medium. The alkynediols are generally dissolved in the aqueous starting mixtures in a concentration of from 10 to 60% by weight. The aqueous mixtures also generally contain from 2 to 8% by weight of impurities, eg. aldehydes, such as formaldehyde and its polymers, acetals or monofunctional alkynols, such as prop-2-yn-1-ol. They may furthermore contain, for example, from 10 to 50% by weight of the saturated diol formed by hydrogenation of the alkynediol. Aqueous mixtures of the stated type are obtained, for example, on a large industrial scale by reacting acetylene with aqueous formaldehyde. During the hydrogenation, the pH of the aqueous starting solution is preferably greater than 6. If the crude butynediol solutions have a lower pH, they can be brought to a pH of greater than 6, preferably from 6.5 to 9, for example by adding an alkali.

The novel process can be carried out using any conventional hydrogenation catalysts, for example the metals which are suitable for catalytic hydrogenation, such as platinum, palladium, ruthenium, nickel, cobalt or copper. Preferred catalysts are those which contain only nickel as the catalytic component. For example, Raney nickel or nickel which is formed by the decomposition of nickel (O) complexes or of nickel formate is particularly preferred. The active metal may also be deposited on a carrier. Other catalysts which can be used for the process are those which contain a plurality of the known hydrogenation metals as active components. The catalyst which consists of nickel, copper and manganese on silica or alumina-containing carriers and is conventionally used for the hydrogenation of butynediol is also suitable. The catalysts are preferably employed in suspended form. For example, they are added in finely divided form to the aqueous medium before the hydrogenation. Instead of metallic nickel, it is also possible to use water-soluble nickel salts of an organic acid of not less than 2 carbon atoms, eg. nickel acetate, nickel propionate or nickel butyrate. The two first-mentioned nickel salts give particularly advantageous results. In this procedure, the nickel salt is added to the aqueous mixture being hydrogenated in an amount such that the said mixture contains nickel in a concentration of from 0.01 to 0.2, preferably from 0.05 to 0.15, % by weight, based on the aqueous alkynediol solution. Although higher concentrations do not have an adverse effect on the reaction, they reduce the cost-efficiency of the process.

Hydrogenation is carried out at above 200° C., eg. from 210° to 280° C., preferably from 230° to 260° C. and under, for example, from 20 to 300, preferably from 50 to 250, bar. Taking into account the expense, pressures beyond the preferred range have no marked advantages. For example, a very pure butanol can be prepared with virtually quantitative selectivity from butynediol over 1% strength by weight Raney nickel in one stage at about 250° C. and under 250 bar. The concentration of the hydrogenation catalyst depends on the desired reaction rate at the selected reaction temperature and is in general, for example, from 0.05 to 5% by weight, which is substantially lower than that in the hydrogenation procedure otherwise carried out. Unsupported catalysts are preferred since they can be separated off readily and completely by decantation or filtration using magnetic and sheet filters, and may furthermore be recycled.

The hydrogenation can be carried out in a simple apparatus, such as a bubble column, a stirred reaction vessel or a circulation reactor, which ensure adequate mass transfer and thorough mixing of the reaction mixture by means of, for example, nozzles.

In the continuous procedure, as carried out in, for example, a stirred reactor or a circulation reactor, the heat of hydrogenation is advantageously used for heating the fresh feed, for example to an initial temperature of from 160° to 180° C., before it enters the reactor. Heating is effected, for example, by means of an external heat exchanger through which recycled reaction mixture flows. The reaction mixture heats up to above 200° C. at the rate at which the hydrogenation progresses along the reaction zone. The final temperature in this case is determined predominantly by the amount of fresh feed and the amount of heat of hydration used, for example, for generating steam.

If not carried out continuously, hydrogenation is preferably effected by a semicontinuous method. In this procedure, the catalyst is suspended in a small portion of the ready-prepared product and the suspension is initially taken. Butynediol solution is then passed continuously into the reaction vessel at the reaction temperature and under the reaction pressure, at the rate at which hydrogenation takes place. This avoids the presence of an excessively high concentration of butynediol in the reaction volume during the hydrogenation.

The hydrogenating metal suspended in the reaction mixture is separated off after the hydrogenation, for example by a conventional physical separation method, such as centrifuging, sedimentation or filtration. The catalysts may be recycled to the reaction space. They retain their initial activity over long reaction times.

If nickel salts are used, metallic nickel is formed under the conditions of the novel process. The nickel suspended in the reaction mixture is separated off after the hydrogenation, for example by a conventional physical separation method, such as centrifuging, sedimentation or filtration. The nickel recovered in this manner can be treated with the appropriate organic acid, such as acetic acid, to convert it to a nickel salt solution, which can be used again for the process according to the invention. The catalyst losses in this procedure are negligible.

The novel process contradicts all previous experience by taking place at temperatures regarded as unsuitable for the reaction, and gives the alkanediols in extremely high purity. The selectivity is virtually 100%. This result is surprising since such an advantageous result in not obtained, for example, when the hydrogenation of the alkynediols is carried out in a conventional manner at below 200° C. The advantageous result was also not to be expected because alkynes are known to be sensitive to high temperatures, and it was to be assumed that the minor constituents (aldehydes and acetals) present in the crude butynediol solutions would form polymeric residues under the effect of such high temperatures and hence produce undesirable deposits on the catalyst. Surprisingly, however, the life of the catalyst is not adversely affected in the hydrogenation according to the invention. For example, the nickel catalyst used under the reaction conditions retains its activity even when it is used repeatedly for the same reaction. Contrary to experience in general, the expected increased formation of butanol and the associated reduction in yield were not observed at high reaction temperatures The amount of residue is only about 10% of the amount produced by the conventional process at a lower temperature.

The butanediol obtainable by the novel process has a low polyester color number, which is usually 40 APHA. According to U.S. Pat. No. 4,213,000, a butanediol possessing such a polyester color number is obtained only when hydrogenation is carried out in two stages, the hydrogenation in the second stage being effected at an acidic pH.

EXAMPLE 1

For the continuous hydrogenation of butyne-1,4-diol, the crude aqueous butyne-1,4-diol solution used was obtained by reacting acetylene with aqueous formaldehyde (for the preparation, see Ullmanns Enzyklopädie der technischen Chemie (1953), volume III, pages 109–119, and volume IV, pages 754–757, German Published Application DAS 2,421,407 and German Laid-Open Application DOS 2,536,273). It consisted of 0.6% by weight of formaldehyde, 0.6% by weight of formaldehyde polymers, 39% by weight of but-2-yne-1,4-diol, from 55 to 60% by weight of water and from 2 to 4% by weight of unidentified acetals and undistillable components.

The hydrogenation was carried out in a vertical reaction tube having a reaction capacity of 1000 parts by volume. The reaction tube had a diameter/length ratio of 1:40 and did not contain any baffles. It was fed from below, the feed flowing into a high-pressure separator at the upper end. The hydrogen was likewise fed in at the lower end of the reaction tubes. The hydrogen pressure at the high-pressure separator and in the reaction tube was 250 bar. From $10^4$ to $10^6$ parts by volume (S.T.P.)/hour of hydrogen were removed as exit gas from the gas phase of the high pressure separator. Nickel acetate was added to the feed consisting of the abovementioned starting solution in such a manner that the aqueous mixture in which the nickel acetate dissolved had a nickel content of 0.1% by weight. The feed was preheated to 180° C. and pumped continuously into the reaction tube. The heat of hydrogenation liberated was removed by means of an internal pipe coil and passed through an external heat exchanger (the heat can also be removed just as successfully in an external cooler by direct cooling by means of a circulated bleed stream of the reaction product). A mean temperature of from 230° to 250° C. was maintained in the reaction tube, into which the solution being hydrogenated was fed at a rate of 150 parts per hour. 150 parts/hour of a reacted mixture were obtained, and this mixture was found to be composed of the following components, calculated as the anhydrous substance:

methanol: 1.0% by weight,
n-butanol: 0.6% by weight,
hydroxybutyraldehyde: 0.01% by weight,
butane-1,4-diol: 97.9% by weight,
methylbutanediol: 0.2% by weight,
acetals: 0.01% by weight,
ethanol: 0.1% by weight,
non-volatile components 0.2% by weight.

After a reaction time of 20 days, it was possible to reduce the feed of fresh nickel acetate to 10% of the initial concentration without having an adverse effect on the hydrogenation. After a reaction time of a few days, metallic nickel appeared in the reacted mixture. This was filtered off using a filter cartridge installed between the reaction tube and the high-pressure separator. After a further 20 days, the reacted mixture was diverted to a metal filter cartridge connected in parallel and then passed into the high-pressure separator. After the first metal filter cartridge had been removed, it was washed with glacial acetic acid and the nickel filtered off was thus converted to nickel acetate. The nickel acetate solution obtained in this manner, if necessary after neutralization with, for example, sodium carbonate, could be used again for further hydrogenations by this process. Apart from mechanical losses, no catalyst consumption was observed.

EXAMPLE 2

The procedure described in Example 1 was followed, the reaction tube being charged with 130 parts/hour of a 60% strength by weight aqueous solution of hex-3-yne-2,5-diol which contained dissolved nickel acetate in an amount such that the nickel content of the solution was 0.1% by weight. Gas chromatographic investigation showed that the reacted mixture consisted of 99.5% by weight of hexane-2,5-diol and only about 0.1% by weight of hexan-2-ol (without taking water into account).

EXAMPLE 3

500 parts by weight of a crude butanediol solution obtained as described in Example 1 were introduced into a stirred pressure vessel having a reaction volume of 5000 parts by volume. 25 parts by weight of Raney nickel were also introduced into the reaction vessel. The apparatus was charged continuously, at 230° C. and under a total pressure of 250 bar (hydrogen pressure and vapor pressure of the reaction system), with 150 parts by weight/hour of the crude butyne-1,4-diol solution described in Example 1 as the starting solution. After passing a pipe coil located in the reaction space, this feed passed into the stirred reactor at an initial temperature of 170° C. A highly exothermic reaction took place immediately. The reaction temperature was maintained at 230°–245° C. by cooling with water under superatmospheric pressure in an internal coil. After 23 hours, the feed was stopped, and hydrogenation was continued for a further 20 minutes in order to complete the reaction. When the reaction mixture was cooled, 3950 parts of a reacted mixture were obtained. This mixture had the composition stated in Example 1 (calculated as anhydrous substance).

When a similar crude butyne-1,4-diol solution having a formaldehyde content of 2% by weight was employed in this example, a reacted mixture having a similar composition and in which the methanol content was about 2% by weight was obtained.

EXAMPLE 4

Example 3 was repeated, except that, instead of Raney nickel, 100 parts of a catalyst obtained by milling catalyst extrudates conventionally used for the hydrogenation of butynediol and composed of 16.5% of nickel, 5% of copper and 0.7% of manganese on a silica gel carrier were used. The crude butynediol solution was converted with virtually quantitative yield. In this case too, a reaction solution was obtained which had the composition described in Example 1.

We claim:

1. A process for the preparation of a very pure alkanediol by hydrogenating an alkynediol in an aqueous medium and in the presence of a hydrogenation catalyst under a hydrogen partial pressure of above 20 bar, wherein the hydrogenation is carried out at from 210° to 280° C.

2. A process as claimed in claim 1, wherein the hydrogenation is carried out using a suspended nickel catalyst.

3. A process as claimed in claim 1, wherein a water-soluble nickel salt of an organic acid of not less than 2 carbon atoms is added to the aqueous mixture to be hydrogenated, and metallic nickel is separated off mechanically from the reaction mixture when the hydrogenation is complete.

4. A process as claimed in claim 1, wherein butane-1,4-diol is prepared from but-2-yne-1,4-diol.

5. A process as claimed in claim 1, wherein hydrogenation is carried out at from 230° to 260° C. and under a hydrogen partial pressure of from 50 to 250 bar.

6. A process as claimed in claim 3, wherein the nickel separated off is treated with an organic acid of not less than 2 carbon atoms to convert it to the nickel salt, and the latter is used directly for the hydrogenation.

7. A process as claimed in claim 1, wherein hydrogenation is carried out at a pH greater than 6.

* * * * *